(12) United States Patent
Harper

(10) Patent No.: US 6,306,305 B1
(45) Date of Patent: Oct. 23, 2001

(54) METHOD AND APPARATUS FOR DIFFUSIVE TRANSFER BETWEEN IMMISCIBLE LIQUIDS

(75) Inventor: Michael Jonathan Harper, London (GB)

(73) Assignee: British Nuclear Fuels plc, Cheshire (GB)

( * ) Notice: Subject to any disclaimer, the term of this patent is extended or adjusted under 35 U.S.C. 154(b) by 0 days.

(21) Appl. No.: 09/171,367
(22) PCT Filed: Apr. 15, 1997
(86) PCT No.: PCT/GB97/01027
    § 371 Date: Apr. 29, 1999
    § 102(e) Date: Apr. 29, 1999
(87) PCT Pub. No.: WO97/39814
    PCT Pub. Date: Oct. 30, 1997

(30) Foreign Application Priority Data

Apr. 19, 1996 (GB) .................................................. 9608129

(51) Int. Cl.[7] .................................................. B01D 11/00
(52) U.S. Cl. ...................... 210/634; 210/321.6; 210/511; 210/644; 216/2
(58) Field of Search .............................. 210/243, 321.84, 210/321.85, 511, 634, 644, 748; 209/1, 155; 422/68.1; 436/180; 216/2, 56

(56) References Cited

U.S. PATENT DOCUMENTS

| 2,705,594 | | 4/1955 | Brewer . | |
|---|---|---|---|---|
| 2,710,250 | * | 6/1955 | Andrews et al. | 210/634 |
| 4,214,981 | * | 7/1980 | Giddings | 210/748 |
| 4,789,468 | * | 12/1988 | Sirkar | 210/137 |
| 4,894,146 | * | 1/1990 | Giddings | 210/748 |
| 5,114,579 | | 5/1992 | Takigawa . | |
| 5,137,637 | * | 8/1992 | Korin | 210/634 |
| 5,141,651 | * | 8/1992 | Giddings | 210/748 |
| 5,193,688 | * | 3/1993 | Giddings | 210/748 |
| 5,204,002 | * | 4/1993 | Belfort et al. | 210/634 |
| 5,252,220 | * | 10/1993 | Coughlin et al. | 210/644 |
| 5,304,487 | * | 4/1994 | Wilding et al. | 210/634 |
| 5,437,799 | * | 8/1995 | Kissler | 210/511 |
| 5,932,100 | * | 8/1999 | Yager et al. | 210/511 |

FOREIGN PATENT DOCUMENTS

| 1289913 | 8/1962 | (FR) . |
| 2196831 | 3/1974 | (FR) . |
| WO 96/12541 | 5/1996 | (WO) . |

* cited by examiner

Primary Examiner—Joseph W. Drodge
(74) Attorney, Agent, or Firm—Crowell & Moring LLP

(57) ABSTRACT

Apparatus for carrying out a process between first and second immiscible fluids comprises channels defining first and second primary flow paths for permitting fluid flow of the respective first and second fluids therethrough. Portions of the flow paths are disposed close to or adjacent one another and communicate with one another at a region where the flow paths are constructed and arranged so as to permit the fluids to form a stable interface between them. At least one of the fluids is induced to flow in a secondary direction perpendicular to the direction of its primary flow path at the region either by bending the primary flow path around a curve, or by positioning flow detectors within the flow path.

31 Claims, 5 Drawing Sheets

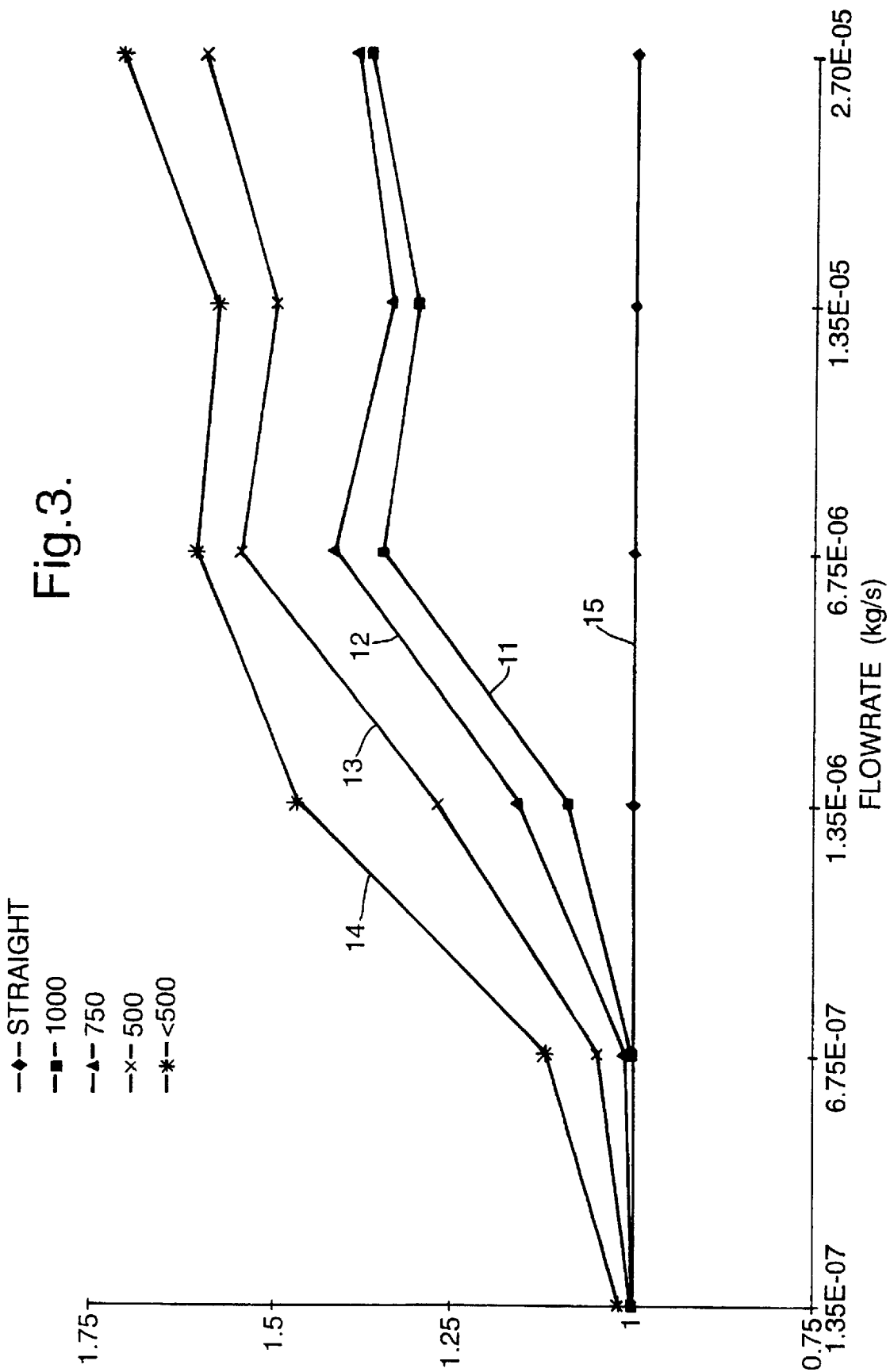

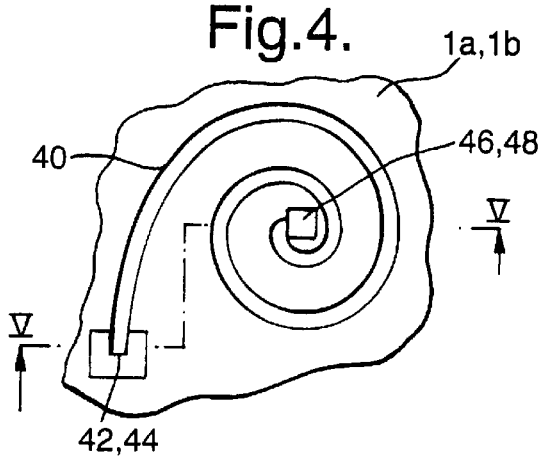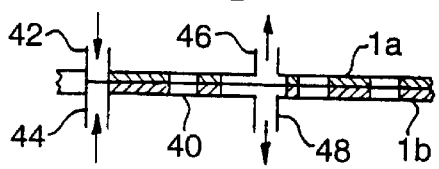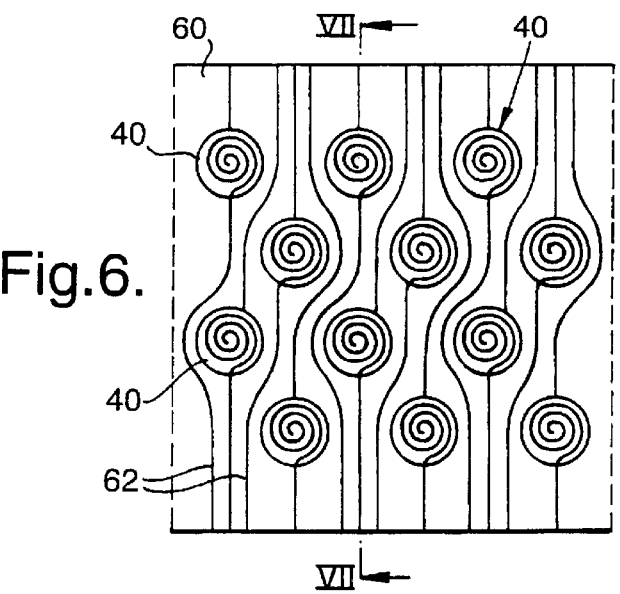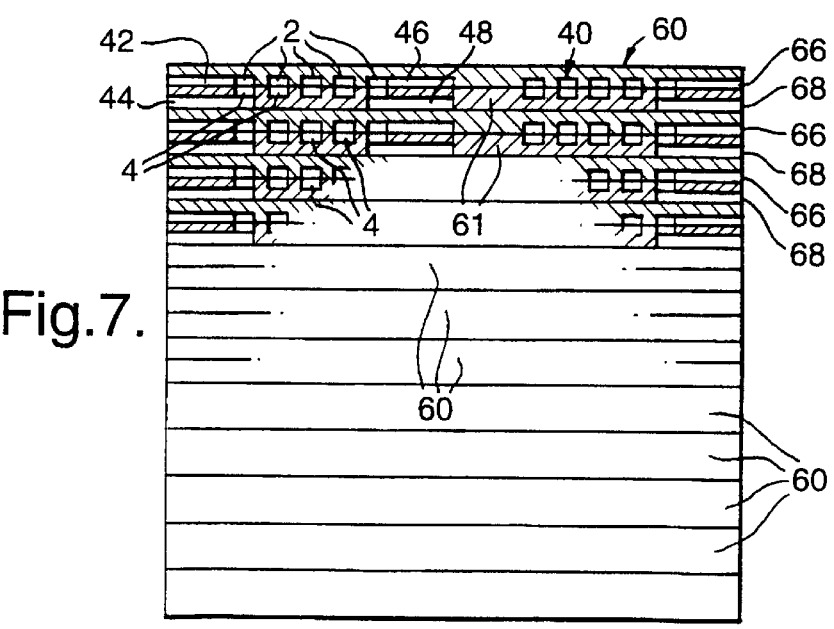

METHOD AND APPARATUS FOR DIFFUSIVE TRANSFER BETWEEN IMMISCIBLE LIQUIDS

This application is a 371 of application PCT/GB97/01027, filed on Apr. 15, 1997

FIELD OF THE INVENTION

The present invention relates to a method and apparatus for carrying out a process between first and second immiscible fluids, for example solvent extraction of a component of one fluid to another fluid.

BACKGROUND ART

In the chemical industry a common technique for purifying or analysing chemicals is an exchange process. Solvent extraction relies upon the preferential transfer of one or more components from one phase (fluid) in which the component (solute) is dissolved into a second immiscible phase. Usually this is accomplished by physical mixing followed by separation of the two phases using gravity. It has been found that the more thoroughly the two phases are mixed, the more rapidly the transfer process proceeds by reason of the greater surface area of the smaller globules of liquid and reduced diffusion distances within the phases. The time for separation of the phases however increases with more thorough mixing, and hence for a desired efficiency of solute transfer, the separation time may become unacceptably long, this being the principal disadvantage of the process.

Our co-pending International Application PCT/GB95/02489 discloses a method and means of bringing first and second immiscible fluids in contact with one another for interaction, while inhibiting physical mixing of the fluids, to permit easy separation of the fluids subsequent to interaction, and claims apparatus for carrying out a process between first and second immiscible fluids. The apparatus comprises first and second flow paths for permitting fluid flow of respective first and second immiscible fluids therethrough. Portions of the flow paths are disposed close to, or adjacent to, one another and communicate with one another in a region which is such as to permit the fluids to form a stable open interface therein. At least the first flow path in the interface region has a width normal to the interface within the range 10 to 500 micrometres.

The International Application also discloses a method of carrying out a process between first and second immiscible fluids, the method comprising:

1) providing first and second flow paths having portions disposed adjacent to or close to one another and communicating with one another in a region in which the fluids can contact one another;
2) flowing the first and second immiscible fluids through respective said first and second flow paths such that, at least in said region, the flow of both fluids is essentially laminar, and a stable open interface is formed between the fluids;
3) permitting significant transfer of a desired component (such as a solute) to another immiscible fluid (such as a solvent) at said interface between the fluids by diffusive transport within the fluids; and
4) flowing the fluids away from the interface region in their respective flow paths without mixing of the fluids.

At the interface region, the flow paths are close to, or adjacent to, one another so that fluid flow through the flow paths continually replenishes the fluid at the interface. An interface is defined at which the fluids contact one another under defined conditions so that the interface remains stable despite movement of the fluids. Turbulence should not be present at the interface in an amount sufficient to disrupt the interface. For efficiency of operation, portions of the fluids should remain in contact with one another in the interface region for a short time so that throughput of fluids can be maximised. The continual renewal of the fluids at the interface has the additional advantages that degradative side reactions between the fluids and their dissolved components, such as hydrolysis of extractant chemicals, is reduced, as is also the accumulation of undesirable products at the interface. The fluid portions should desirably remain in contact with one another for a period of the order of between 1 and 100 seconds, or more generally between 0.1 and 100 seconds.

It is an object of the present invention to improve the conditions for diffusive transport to take place and encourage a more efficient transport across the interface between the two fluids.

According to one aspect of the present invention there is provided an apparatus for carrying out a process between first and second immiscible fluids comprising first and second channels defining primary flow paths for permitting fluid flow of the respective first and second fluids therethrough, portions of said channels being disposed close to or adjacent one another and constructed to communicate with one another to define a region, where a stable interface is formed between the fluids, and secondary flow inducing means, which is operable, in use, to induce at least one of the fluids to flow in a secondary direction perpendicular to the direction of the primary flow path at said region.

Preferably the secondary flow inducing means comprises constructing at least one of the channels to extend around a curve at said region. Both of the first and second channels may be curved at said region.

In an alternative embodiment the secondary flow inducing means comprises flow deflectors positioned within at least one of the channels, or both of the channels.

The, or each channel may be a spiral channel defining a spiral primary flow path.

According to one aspect of the present invention there is provided an apparatus for carrying out a process between first and second immiscible fluids, comprising first and second channels defining respectively first and second primary flow paths for permitting fluid flow of the respective first and second immiscible fluids therethrough, portions of the channels being disposed close to or adjacent one another and constructed to communicate with one another to define a region where, in use, a stable interface is formed between the first and second fluids, at least the first channel at said region being curved so that, in use, the fluid flow therein has a curved trajectory in a direction along the primary flow path which generates a secondary circulation of the fluid in a direction perpendicular to the direction of the primary flow path.

In a further aspect of the present invention there is provided an apparatus for carrying out a process between first and second immiscible fluids, comprising a stacked structure of adjacent plates, each adjacent pair of plates defining one or more pairs of first and second channels defining primary flow paths for permitting fluid flow of the respective first and second immiscible fluids therethrough, portions of the channels being disposed close to or adjacent one another and constructed to communicate with one another to define a region where, in use, a stable interface is formed between the first and second fluids, and wherein at least the, or each first channel is curved at said region so that, in use, the fluid flow therein has a curved trajectory in a direction along the primary flow path and generates a secondary circulation of the fluid in a direction perpendicular to the direction of the flow path. Preferably strcture of plates is held together by the application of a compressive force.

Preferably the flow rate Q of each of the fluids are between 6.75 E-07 and 1.35 E-05 kg/s, and the flow rate Q is given by:

$$Q = K l^4 \Delta P / \mu L,$$

where $\Delta P$ is the pressure drop along a unit length, L, of the flow paths, $\mu$ is the viscosity of the fluid, l, is the width of the flow path and K is a constant.

According to a further aspect of the present invention there is provided a method of carrying out a process between first and second immiscible fluids, the method comprising: the steps of:

a) providing first and second flow paths having portions disposed adjacent to or close to one another and communicating with one another to defme a region where, in use, the fluids can contact one another;

b) flowing the first and second immiscible fluids along respective said first and second primary flow paths such that, at least in said region, the flow of both fluids is essentially laminar and, a stable interface is formed between the fluids;

c) simultaneously causing at least one of the fluids to flow in a direction perpendicular to the primary path flow;

d) permitting significant transfer of a desired component of at least one of the fluids to the other fluid at said interface between the fluids by diffusive transport within the fluids without mixing of the fluids; and e) flowing the fluids away from the interface region in their respective flow paths.

Preferably the step (c) is achieved by causing the flow of fluid to flow along a primary flow path that extends around a curve. The curve is preferably a spiral curve.

Alternatively the step (c) is achieved by means of angled flow deflectors positioned within the, or each, channel.

A foraminated membrane may be provided at the interface between the fluids. If desired the flow deflectors may be fin mounted on one or both sides of the membrane.

In accordance with the invention, an enhanced diffusive transport between the two fluids is achieved by reason of the circulation of the fluid perpendicular to the direction of flow, since this acts to bring fresh regions of fluid into the interface region; diffusion will take place at increased efficiency when the difference in concentration of the component between the two fluids is maintained high. The precise mechanism by which circulation is achieved will be explained in more detail below.

DESCRIPTION OF THE PREFERRED EMBODIMENT

A preferred embodiment of the invention will now be described with reference to the accompanying drawings, in which:

FIG. 3 is a graph indicating diffusive transfer rates plotted against. pressure drop in the apparatus of FIGS. 1 and 2 for various radii of curvature of the flow path;

FIG. 4 is schematic plan view of a second implementation of the preferred apparatus;

FIG. 5 is a cross sectional view of the apparatus of FIG. 4 taken along line V—V of FIG. 4;

FIG. 6 shows a third embodiment of the invention in the form of a stacked structure and shows schematically a plan view of one of the etched surfaces of a plate forming one of the layers of the stack;

FIG. 7 illustrates schematically a cross sectional view of the stacked structure of FIG. 6 and shows in greater detail a cross sectional view taken along line VII—VII of one pair of the stacked plates forming one of the layers of the apparatus of FIG. 6.

FIG. 8 is a view looking in the direction of arrows VIII—VIII of FIG. 9;

DESCRIPTION OF THE PREFERRED EMBODIMENT

Figure 1:
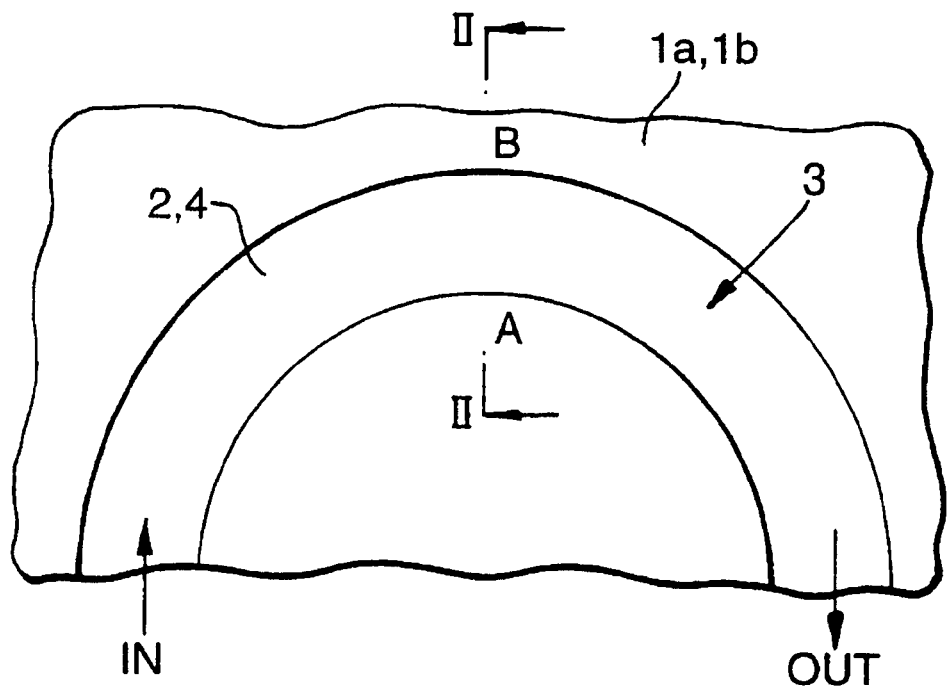
FIG. 1 is a top plan view of a preferred embodiment of apparatus according to the invention.
Figure 2:
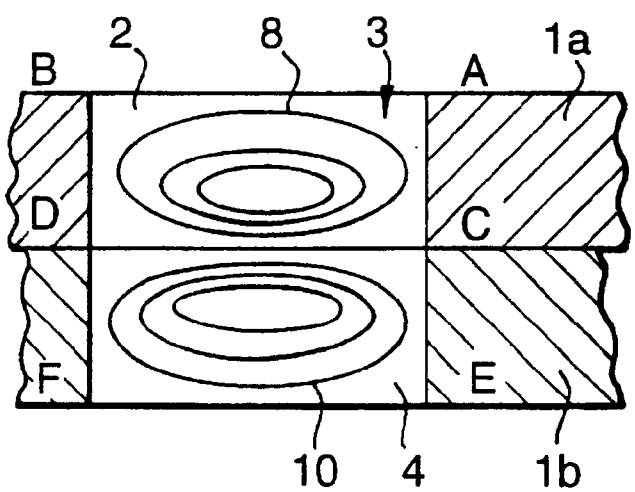
FIG. 2 is a cross-sectional view of the apparatus of FIG. 1 along the line II—II of FIG. 1, showing circulation paths for fluids therein.

Referring to the drawings, FIGS. 1 and 2 show schematically, apparatus comprising two silicon plates 1a, 1b which have their confronting surfaces etched to form channels 2,4 defining two discrete flow paths 2, 4 which merge (as shown in FIG. 2) to define a region 3 where a stable interface is formed between the first and second fluids. The channels 2, 4 are typically rectangular channels of 100×100 micrometers cross-section, and the interface region 3 extends for a length typically of approximately 1.9 mm along the direction of the flow paths 2,4. The fluid in flow path 2 is aqueous and that in flow path 4 is an organic fluid which is heavier than the fluid in flow path 2. In this specific example, the inner surfaces of the flow paths 2, 4 are respectively hydrophilic and hydrophobic, in order to maintain the fluids in the respective flow paths 2, 4 and to maintain a stable open interface 6 between the fluids in the interface region 3 to enable diffusive transport of a solute across the interface.

An essential feature of the present invention is the provision of a means for inducing a one or both of the fluids flowing in flow paths 2, 4, to swirl in a secondary direction perpendicular to it's primary, direction of flow along it's respective flow path. In this way, the transfer ratio can be greatly enhanced, as discussed below, without destroying the laminar flow of the fluids at their interface.

This secondary flow can be induced in a number of ways. In FIG. 1 it is achieved by constructing and arranging the channels 2,4, at the region where the interface between the fluids is formed, as a semicircular curve of approximately 500 micrometers radius which extends along the direction of the flow paths 2, 4 a distance of approximately 1.9 mm. In operation, as fluid flows around the semicircular channel, it experiences an inertial centrifugal force. As indicated in FIG. 2, fluid flowing along the outside of the bend (line ACE) is at a higher pressure than around the inside of the bend (line BDF). Adjacent to the upper wall AB and lower wall EF the velocity is reduced by the viscous action of the boundary layers there, and consequently, the increase in pressure from the inner to the outer radius is less in the upper and lower boundary layers (AB and EF) than along the interface 6 (centre line CD). Since the pressure at C is greater than at A and E, and the pressure at D is less than at B and F, a secondary circulatory flow is induced in the fluids in a radial plane perpendicular to the direction of flow along the channels 2,4, as shown by the lines 8, 10.

In the specific example, the upper and lower channels 2, 4 are filled with lighter and heavier immiscible phases respectively. Therefore the secondary recirculation will enhance the stability of the interface (CD) and increase the propensity for mass transfer by constantly renewing the interface.

In a modification, a porous membrane is positioned at the interface 6, for example in the form described in our co-pending application PCT/GB95/02488.

Referring to FIG. 3, the graph summarises the effect that increasing flow rate and tightening the bend radius has on transfer due to the convective recirculation. The curves 11, 12, 13, 14 are for various bend radii (respectively 1000, 750, 500, >500 micrometres), for equal channel lengths, each 1.9 mm long. The channels defining the fluid flow paths are each of rectangular section with sides of 100 micrometres. The vertical axis of the graph shows the transfer ratio, and quantifies the enhancement above diffusion only transfer along a straight flow path (shown as curve 15). This indicates that the optimum flow rates at which the secondary recirculation becomes significant, are in the region of 6.5 E-07 and 1.5 E-05 kg/s over a channel length of 1.9 mm. The graph also shows that the tighter the curve of the channels 2, 4, the greater will be the transfer for any given pressure drop. For flow rates higher than 1.35 E-05 kg/s, the enhancement drops off slightly only to increase exponentially as the flow becomes turbulent, breaking the laminar transfer conditions.

It will be understood that flow rate Q is related to the length L of the channel, the width 1, of the channel, the pressure drop $\Delta P$ along the length of the channel, and the viscosity $\mu$, as follows:

$$Q = K(l)^4 \Delta P / \mu L,$$

where K is a proportionality factor

It may also be shown that the conditions for the fluid flow to remain laminar, before the onset of turbulence, are given for flow rates Q as follows:

$$Q < 2.0 \times 10^3 \, \mu l / L \rho$$

where $\rho$ is the density of the fluid.

Thus it is possible to relate by means of the above two equations the preferred range of flow rates as given above, to any of the other variable of the system.

Referring to FIGS. 4 to 7, these show various implementations of the embodiments of the invention shown in FIGS. 1 and 2. In FIGS. 4 and 5, the channels 2, 4 are etched in the confronting surfaces of two silicon plates 1(*a*), 1(*b*), and each is constructed in the form of a spiral at the region 3, where the interface between the fluids is formed. Each channel 2, 4, has a cross-section similar to that shown in FIG. 2. The Channels 2, 4 have inlets 42, 44, for aqueous and organic liquids respectively, and outlets 46, 48 for aqueous and organic liquids respectively.

In FIGS. 6 and 7, a stacked structure is shown comprising a plurality of pairs of silicon plates 60, 61 (only one pair of which is shown in detail, but the other pairs of plates are of identical construction). Each pair of plates 60, 61, has channels etched on their confronting surfaces to define an array of spiral structures 40, of a similar construction to that shown schematically in FIG. 4. The spiral structures are interconnected by channels 62. Adjacent pairs of plates 60, 61 form a contactor arrangement. aqueous and organic liquids are input respectively to the inputs 42 and 44 of the adjacent plates, and output in a similar manner from the outputs 66, 68. The individual plates 60, 61 in the stack may have channel or manifold geometries etched or otherwise formed in one or both of their planar surfaces, and each pair of plates 60,61 constitutes a layer in the stack. These layers are pressed together such that flow channels are formed between the etched confronting surfaces of the plate 60, 61 of each pair of plates and/or between etched surfaces and flat surfaces of adjacent layers.

Adjacent layers in such an arrangement may be physically bonded together. However, it is desired, and in accordance with the invention, to align the layers in the stack, and then to subject the stack to a compressive pressure force in order to form a liquid-tight seal between adjacent layers. In this way there is provided a means of cleaning up micro-contactors (or indeed "conventional" micro-reactors) which may become clogged, scratched, or otherwise damaged during service by disassembling the stack.

The advantages of this approach are:

(a) The sealing process is more reliable than bonding, and would also seal a large number of layers together in a single step (thus replacing many separate bonding processes).

(b) If the system is one which causes the surfaces of the channels to deteriorate over a period of operation, for instance due to accumulation of debris or loss of surface finish, then the stack could be taken out for repair, and the layers separated simply by removing the sealing force. The substrates themselves could then be "refurbished" by means of an appropriate process, e.g. chemical removal of debris, or plasma polishing of the surfaces, and the layers re-aligned and re-formed into an operating stack.

(c) Alternatively, if only a limited number of substrates are damaged, these could be identified, removed and replaced with new ones, and the stack then re-formed. This would allow most of the layers in the stack to be re-used.

(d) For many systems, particularly if the channels are made from - or lined with-high-value materials, this approach is cost-effective compared with disposal of the stack and replacement with a brand new one.

(e) In some "batch" processes with small throughputs it may be practical to allow the component of the fluid to accumulate in the outlets 66, 68 of the stack, (or provide reservoirs in the outlet channels of the stack, to collect the component) and to disassemble to stack to recover the collected component of the fluid.

Figure 8:
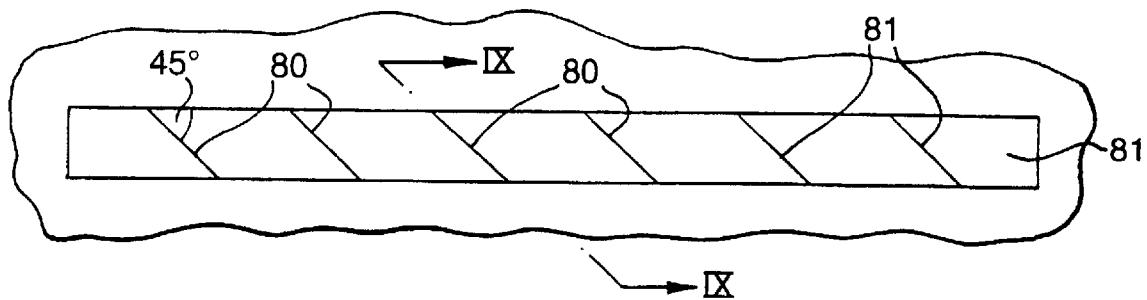
FIG. 8 is a plan view looking into one of the channels of another embodiment of the invention.
Figure 9:
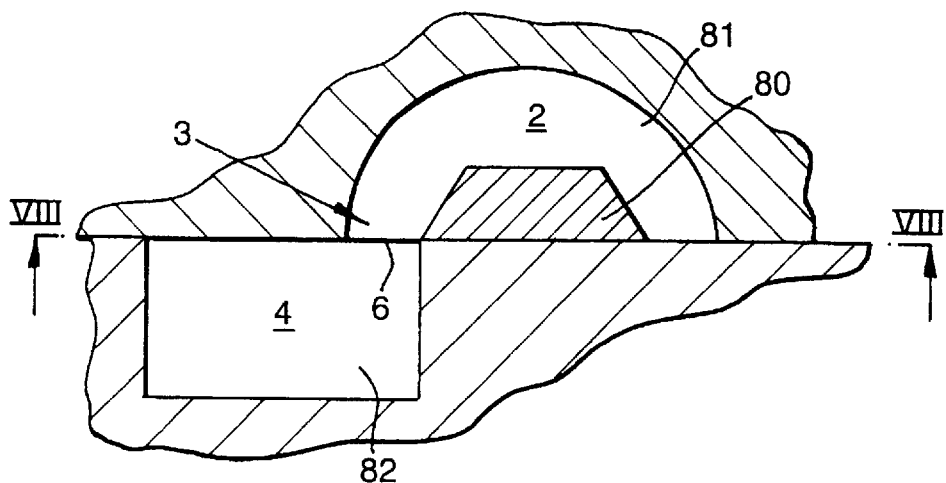
FIG. 9 is a cross sectional view taken along line IX—IX of FIG. 8.
Figure 10:
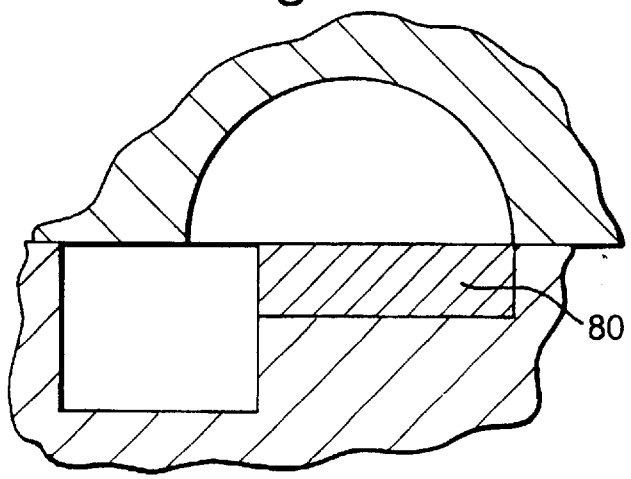
FIG. 10 is a cross sectional view of the channels of a further embodiment of the invention similar to that of FIG. 9

In the above described embodiments the secondary flow inducement was achieved by curving the primary flow paths 2, 4. In the embodiments of FIGS. 8 to 10 the secondary flow is induced by means of flow deflectors Referring in particular to FIGS. 8 and 9 there is shown an interface region 3 in which the flow paths 2, 4 are straight but in which flow deflectors 80, in one of the flow paths 2, are employed to cause the fluids to swirl along the flow path. From FIG. 8 it will be seen that the channel 2, is formed by etching a semicircular cross-sectional shape groove into the surface of one of the silicon plates 1(*a*). The diameter of the channel 81 is typically 100 μm. Swirl is induced in the fluid flowing along channel 81 by positioning small fins 80 inclined at an angle of 45° to the primary flow direction at 200 μm intervals along the channel 4. The fins 80 are positioned centrally in the channel 81 and project 20 μm into the channel 81. Each fin 80 is of trapezoidal shape and has a base 60 μm and a extremity 40 μm long. Channel 4, is formed by etching a rectangular groove in the surface of the other plate 1(*b*). Channel 4 is typically 100×100 μm and is offset from channel 2 to form an interface region 3 of approximately 20 μm wide extending along the length of the channels 2, 4 for a distance of about 1.9 mm. In the version shown in FIGS. 8 and 9, the fins 80 are formed by etching away the surface of plate 1(*b*) to leave thin fins standing proud. This is difficult to do without the risk of damaging the fins 80. It may be possible to form the fins 80 on a porous membrane 82 of the type described in our co-pending International Patent Application No. PCT/GB/95/-2488. The fins 80 may also be provided upstream and downstream of the interface region 3.

In operation, fluid flowing along each channel 2, is induced to swirl by the fins 80 (in an anti clockwise direction as viewed in FIG. 9), and fluid flowing along channel 4 flows axially to cause a laminar flow of the two fluids at their interface 6 without mixing of the fluids.

Referring to FIG. 10 the fins are formed by etching away the surface of the plates 1(*b*) and the spaces between the fins communicates with the side of the channel 2 for a depth of 20 μm.

Figure 11:
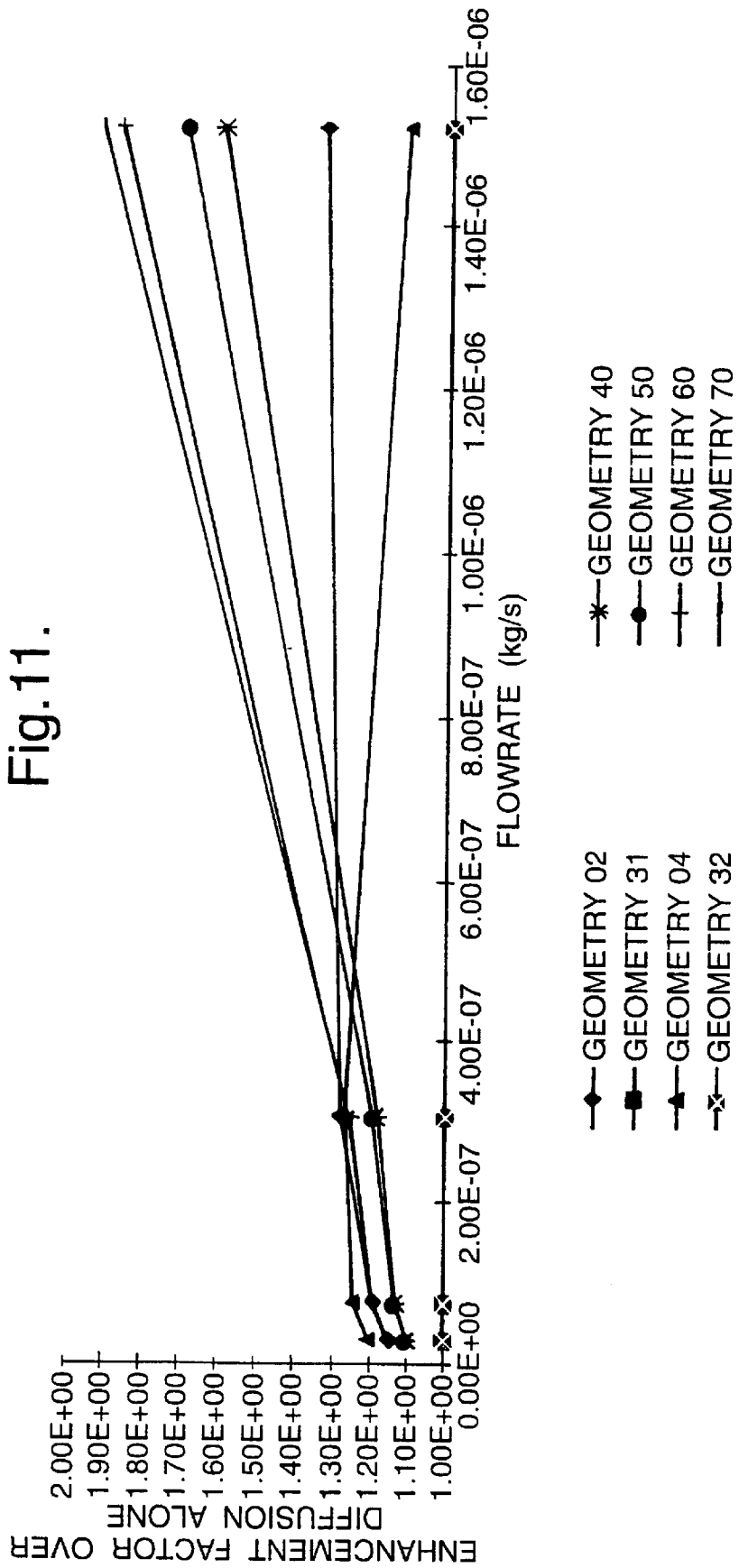
FIG. 11 is a graph of the transfer ratio of a number of different geometries of secondary flow inducers (two with fins, two with curved channels,) plotted against flow rates in kg/s compared with geometries without secondary flow inducers.

In the embodiment shown in FIG. 1 the interface region of the channels 2,4 extend around a semicircular curve (subtending an angle of 180 degrees). It is to be understood that the region 3 may extend more or less than 180 degrees and may be of smaller or larger radius. For example, experimental research has been conducted with channels extending 225 degrees arounda radius of 414 μm and in another example around 350 degrees around a radius of 213 μm Indeed spiral versions have been studied with spirals similar to that shown in FIG. 4 extending from a radius of 500 μm at the inlet to 2500 μm at the outlet curved around an angle of 450 degrees Referring to FIG. 11 there is shown a graph of the transfer ratios of various designs of channels constructed in accordance with the present invention plotted against flow rates. The curves shown are for the following geometries which give the same flow path lengths of 1300 μm.

| Geometry | Description |
|---|---|
| 02 | FIG. 8 |
| 04 | FIG. 9 |
| 31 | Same as FIG. 8 without the fins 80 |
| 32 | Same as FIG. 9 without the fins 80 |
| 40 | Similar to FIG. 1 180°curve around 414 m radius |
| 50 | Similar to FIG. 1 but 225°curve around 331 m radius |
| 60 | Similar to FIG. 1 but 350°curve around 213 m radius |
| 70 | Similar to FIG. 4 but radius at inlet = 50 μm, outlet radius = 2500 μm, and curve = 440°. |

The following table gives further details of the experimental results shown in FIG. 10, and from this it will be seen that at flow rates between 4.00E-07 and 1.60E-06 kg/s geometry 70 performed the best with, in descending order geometries 60, 50, 40, 02 and 04 all better than the geometries 31 and 32.

TABLE

| Run # | Delta P | Flowrate (kg/s) | Geometry 02 | Geometry 31 | Geometry 04 | Geometry 32 | Geometry 40 | Geometry 50 | Geometry 60 | Geometry 70 |
|---|---|---|---|---|---|---|---|---|---|---|
| Total scalar transfer | | | | | | | | | | |
| m17 | 100 | 3.06E − 08 | 1.12E − 01 | 9.75E − 02 | 9.42E − 02 | 7.80E − 02 | 1.07E − 01 | 1.08E − 01 | 1.12E − 01 | 1.13E − 01 |
| m11 | 250 | 7.64E − 08 | 7.19E − 02 | 6.03E − 02 | 6.03E − 02 | 4.83E − 02 | 6.82E − 02 | 6.87E − 02 | 7.16E − 02 | 7.26E − 02 |
| m12 | 1000 | 3.06E − 07 | 3.85E − 02 | 2.99E − 02 | 2.95E − 02 | 2.32E − 02 | 3.54E − 02 | 3.58E − 02 | 3.77E − 02 | 3.78E − 02 |
| m13 | 5000 | 1.52E − 06 | 1.63E − 02 | 1.22E − 02 | 9.85E − 03 | 8.82E − 03 | 1.95E − 02 | 2.07E − 02 | 2.28E − 02 | 2.34E − 02 |
| Total scalar transfer normalised to diffusive only transfer | | | | | | | | | | |
| m17 | 100 | 3.06E − 08 | 1.1.15E + 00 | 1.00E + 00 | 1.21E + 00 | 1.00E + 00 | 1.10E + 00 | 1.11E + 00 | 1.15E + 00 | 1.16E + 00 |
| m11 | 250 | 7.64E − 08 | 1.19E + 00 | 1.00E + 00 | 1.25E + 00 | 1.00E + 00 | 1.13E + 00 | 1.14E + 00 | 1.19E + 00 | 1.20E + 00 |
| m12 | 1000 | 3.06E − 07 | 1.29E + 00 | 1.00E + 00 | 1.27E + 00 | 1.00E + 00 | 1.18E + 00 | 1.20E + 00 | 1.26E + 00 | 1.26E + 00 |
| m13 | 5000 | 1.52E − 06 | 1.34E + 00 | 1.00E + 00 | 1.12E + 00 | 1.00E + 00 | 1.60E + 00 | 1.70E + 00 | 1.87E + 00 | 1.92E + 00 |

What is claimed is:

1. Apparatus for carrying out a process between first and second immiscible fluids comprising first and second channels constructed to define primary flow paths for permitting parallel and co-current fluid flow of the respective first and second fluids therethrough white inhibiting mixing of the fluids, portions of said channels being disposed close to or adjacent one another and constructed to communicate with one another to define a region, where a stable interface is formed between the fluids, and secondary flow inducing means, which is operable, in use, to induce at least one of the fluids to flow in a secondary direction perpendicular to the direction of the primary flow path at said region.

2. Apparatus according to claim 1 wherein the secondary flow inducing means comprises constructing at least one of the channels to extend around a curve at said region.

3. Apparatus according to claim 2 wherein both of the first and second channels are curved at said region.

4. Apparatus according to claim 1 wherein the secondary flow inducing means comprises flow deflectors positioned within at least one of the channels.

5. Apparatus according to claim 4, wherein a foraminated membrane is provided at the interface between the fluids, and said flow deflectors are provided on one or more sides of the membrane.

6. Apparatus according to claim 1 wherein the, or each channel is a spiral channel defining a spiral primary flow path.

7. Apparatus according to claim 6 wherein a foraminated membrane is provided at the interface between the fluids, and flow deflectors are provided on one or more sides of the membrane.

8. Apparatus according to claim 1 wherein a secondary flow is induced in a first direction in the first fluid and a secondary flow is induced in the second fluid in a different direction to the first direction.

9. Apparatus according to claim 1 wherein a foraminated membrane is provided at the interface between the first and second fluids.

10. Apparatus according to claim 1, wherein said primary flow paths of said first and second immiscible fluids at said stable interface are essentially laminar.

11. Apparatus for carrying out a process between first and second immiscible fluids, comprising first and second channels constructed to define respectively first and second primary flow paths for permitting parallel and co-current fluid flow of the respective first and second immiscible fluids therethrough while inhibiting mixing of the fluids, portions of the channels being disposed close to or adjacent one another and constructed to communicate with one another to define a region where, in use, a stable interface is formed between the first and second fluids, at least the first channel at said region being curved so that, in use, the fluid flow therein has a curved trajectory in a direction along the primary flow path which generates a secondary circulation of the fluid in a direction perpendicular to the direction of the primary flow path.

12. Apparatus according to claim 11 wherein the, or each channel is a spiral channel defining a spiral primary flow path.

13. Apparatus according to claim 11 wherein the flow rates Q of each of the fluids are between 6.75 E-07 and 1.35 E-05 kg/s, and the flow rate Q is given by:

$$Q = Kl^4 \Delta P / \mu L,$$

where $\Delta P$ is the pressure drop along a unit length, L, of the flow paths, $\mu$ is the viscosity of the fluid, l, is the width of the flow path and K is a constant.

14. Apparatus according to claim 11 wherein a secondary flow is induced in a first direction in the first fluid and a secondary flow is induced in the second fluid in a different direction to the first direction.

15. Apparatus according to claim 11 wherein a foraminated membrane is provided at the interface between the first and second fluids.

16. Apparatus for carrying out a process between first and second immiscible fluids, comprising a stacked structure of adjacent plates, each adjacent pair of plates defining one or more pairs of first and second channels defining primary flow paths for permitting fluid flow of the respective first and second immiscible fluids therethrough, portions of the channels being disposed close to or adjacent one another and constructed to communicate with one another to define a region where, in use, a stable interface is formed between the first and second fluids, and wherein at least the, or each first channel is curved at said region so that, in use, the fluid flow therein has a curved trajectory in a direction along the primary flow path and generates a secondary circulation of the fluid in a direction perpendicular to the direction of the flow path.

17. Apparatus according to any one of claims 1–6, 11 or 16 wherein the flow rates Q of each of the fluids are between 6.75 E-07 and 1.35 E-05 kg/s, and the flow rate Q is given by:

$$Q = Kl^4 \Delta P / \mu L,$$

where $\Delta P$ is the pressure drop along a unit length, L, of the flow paths, $\mu$ is the viscosity of the fluid, l, is the width of the flow path and K is a constant.

18. Apparatus according to claim 17 wherein a foraminated membrane is provided at the interface between the fluids, and flow deflectors are provided on one or more sides of the membrane.

19. Apparatus according to claim 16 wherein the stacked structure of plates is held together by the application of a compressive force.

20. Apparatus according to claim 19 wherein a foraminated membrane is provided at the interface between the fluids, and flow deflectors are provided on one or more sides of the membrane.

21. Apparatus according to claim 16 wherein the, or each channel is a spiral channel defining a spiral primary flow path.

22. Apparatus according to claim 16 wherein the flow rates Q of each of the fluids are between 6.75 E-07 and 1.35 E-05 kg/s, and the flow rate Q is given by:

$$Q = Kl^4 \Delta P / \mu L,$$

where $\Delta P$ is the pressure drop along a unit length, L, of the flow paths, $\mu$ is the viscosity of the fluid, l, is the width of the flow path and K is a constant.

23. Apparatus according to claim 16 wherein a secondary flow is induced in a first direction in the first fluid and a secondary flow is induced in the second fluid in a different direction to the first direction.

24. Apparatus according to claim 16 wherein a foraminated membrane is provided at the interface between the first and second fluids.

25. A method of carrying out a process between first and second immiscible fluids, the method comprising: the steps of:
   a) providing first and second flow paths having portions disposed adjacent to or close to one another and communicating with one another to define a region where, in use, the fluids can contact one another;
   b) flowing the first and second immiscible fluids along respective said first and second primary flow paths such that, at least in said region, the flow of both fluids is essentially laminar and, a stable interface is formed between the fluids;
   c) simultaneously causing at least one of the fluids to flow in a direction perpendicular to the primary path flow;
   d) permitting significant transfer of a desired component of at least one of the fluids to the other fluid at said interface between the fluids by diffusive transport within the fluids without mixing of the fluids; and
   e) flowing the fluids away from the interface region in their respective flow paths.

26. A method according to claim 25 wherein the step (c) is achieved by causing the flow of fluid to flow along a primary flow path that extends around a curve.

27. A method according to claim 26 wherein the curve is a spiral.

28. A method according to claim 27 wherein the flow rates Q of the fluids are each between 6.75 E-07 and 1.35 E-05 kg/s, and the flow rate Q is given by:

$$Q = l^4 \Delta P / \mu L,$$

where $\Delta P$ is the pressure drop along a unit length, L, of the flow paths, $\mu$ is the viscosity of the fluid, and, L, is the width of the flow path.

29. A method according to claim 26 wherein the flow rates Q of the fluids are each between 6.75 E-07 and 1.35 E-05 kg/s, and the flow rate Q is given by:

$$Q = l^4 \Delta P / \mu L,$$

where $\Delta P$ is the pressure drop along a unit length, L, of the flow paths, $\mu$ is the viscosity of the fluid, and, L, is the width of the flow path.

30. A method according to claim 25 wherein the step (c) is achieved by using angled flow deflectors positioned within the, or each, channel.

31. A method according to claim 25 wherein the flow rates Q of the fluids are each between 6.75 E-07 and 1.35 E-05 kg/s, and the flow rate Q is given by:

$$Q = l^4 \Delta P / \mu L,$$

where $\Delta P$ is the pressure drop along a unit length, L, of the flow paths, $\mu$ is the viscosity of the fluid, and, L, is the width of the flow path.

* * * * *